United States Patent
Bristow

(10) Patent No.: US 9,629,370 B1
(45) Date of Patent: Apr. 25, 2017

(54) SYNERGISTIC HERBICIDAL COMPOSITION AND USE THEREOF

(71) Applicant: ROTAM AGROCHEM INTERNATIONAL COMPANY LIMITED, Chai Wan, Hong Kong (CN)

(72) Inventor: James Timothy Bristow, Hong Kong (CN)

(73) Assignee: ROTAM AGROCHEM INTERNATIONAL COMPANY LIMITED, Chai Wan (HK)

( * ) Notice: Subject to any disclaimer, the term of this patent is extended or adjusted under 35 U.S.C. 154(b) by 0 days.

(21) Appl. No.: 14/955,550

(22) Filed: Dec. 1, 2015

(51) Int. Cl.
*A01N 41/10* (2006.01)
*A01N 47/36* (2006.01)

(52) U.S. Cl.
CPC ............. *A01N 47/36* (2013.01); *A01N 41/10* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,263,440 A * | 4/1981 | Handte | ................ | C07D 235/26 504/267 |
| 4,668,277 A * | 5/1987 | Yamamoto | ............. | A01N 47/36 504/215 |
| 5,550,238 A * | 8/1996 | Chiang | ................ | C07D 521/00 544/206 |
| 6,046,134 A * | 4/2000 | De Gennaro | .......... | A01N 41/10 504/133 |
| 6,420,381 B1 * | 7/2002 | Muraoka | .............. | C07D 471/04 514/300 |
| 7,968,498 B2 * | 6/2011 | Threewitt | .............. | A01N 41/10 504/118 |
| 2006/0196115 A1 * | 9/2006 | Threewitt | .............. | A01N 41/10 47/58.1 R |
| 2015/0031877 A1 * | 1/2015 | Hiratsuka | .............. | A01N 43/84 544/105 |

FOREIGN PATENT DOCUMENTS

WO WO 2006/021743 * 3/2006

OTHER PUBLICATIONS

McClurg, R.B., "X-Ray Powder Diffraction (XRPD) to Describe Crystal Forms," Publication of SSCI an Aptuit Company, Jul. 9, 2008, pp. 1-23.*
Roberts, R.M. et al. Modern Experimental Organic Chemistry. Holt, Rinehart and Winston, New York, 1979, pp. 49-58.*
Anonymous: '2.2 Recrystallization'. PDF [online], published online in Mar. 2011. [retrieved on Sep. 14, 2016]. Retrieved from the Internet<URL: https://yvesrubin.files.wordpress.com/2011/03/recrystallization.pdf>.*
HCAPLUS abstract 1999:261209 (1999).*
Herbicide Handbook, Weed Science Society of America, Seventh Edition—1994, p. 318.
Calculating Synergistic and Antagonistic Responses of Herbicide Combinations; S. R. Colby, Weeds, vol. 15, No. 1 (Jan. 1967), pp. 20-22, Weed Science Society of America and Allen Press.

* cited by examiner

Primary Examiner — John Pak
(74) Attorney, Agent, or Firm — Dickinson Wright PLLC

(57) ABSTRACT

A herbicidal composition is provided, the composition comprising: (A) the crystalline modification I of 2-(4-mesyl-2-nitrobenzoyl)cyclohexane-1,3-dione (mesotrione); and (B) the crystalline modification I of methyl 3-chloro-5-(4,6-dimethoxypyrimidin-2-ylcarbamoylsulfamoyl)-1-methylpyrazole-4-carboxylate (halosulfuron-methyl). A method of controlling plant growth at a locus comprises applying to the locus herbicidally effective amounts of both (A) the crystalline modification I of 2-(4-mesyl-2-nitrobenzoyl)cyclohexane-1,3-dione (mesotrione); and (B) the crystalline modification I of methyl 3-chloro-5-(4,6-dimethoxypyrimidin-2-ylcarbamoylsulfamoyl)-1-methylpyrazole-4-carboxylate (halosulfuron-methyl).

32 Claims, 4 Drawing Sheets

SYNERGISTIC HERBICIDAL COMPOSITION AND USE THEREOF

BACKGROUND

1. Field

The present disclosure relates to a synergistic herbicidal composition containing mesotrione and halosulfuron-methyl, each in particular crystal modifications. The composition finds use in controlling the growth of undesirable plant, particularly in crops, including using the aforementioned composition.

2. Description of Related Art

The protection of crops from undesirable plant, which inhibits crop growth, is a constantly recurring problem in agriculture. To solve this problem, researchers are trying to produce an extensive variety of chemicals and chemical formulations effective in the control of such undesirable growth. Chemical herbicides of many types have been disclosed in the literature and a large number are in commercial use.

Some herbicidal active ingredients have been shown to be more effective when applied in combination rather than applied individually, this effect being referred to as "synergism." According to Herbicide Handbook of the Weed Science Society of America, Seventh Edition, 1994, page 318, "synergism" is an interaction of two or more factors such that the effect when combined is greater than the predicted effect based on the response to each factor applied separately.

The compound 2-(4-mesyl-2-nitrobenzoyl)cyclohexane-1,3-dione has the common name mesotrione. Mesotrione is a substance that can form polymorph crystals. Two different forms, crystalline modifications I and II, of mesotrione are described in WO2006021743, which is incorporated herein by reference for all purposes. Mesotrione is active as a herbicide and is now commercially available in a range of formulations for controlling the growth of undesirable plant.

The compound methyl 3-chloro-5-(4,6-dimethoxypyrimidin-2-ylcarbamoylsulfamoyl)-1-methylpyrazole-4-carboxylate, having the common name halosulfuron-methyl, is a known herbicide.

Halosulfuron-methyl controls annual broad-leaved weeds and nutsedge species, in maize, sugarcane, rice, sorghum, nuts and turf. It can be manufactured by the process described in U.S. Pat. No. 4,668,277, which results in a compound that is present in an amorphous state which is highly viscous. Due to its viscosity, the amorphous state of halosulfuron-methyl has a poor spray equipment clean-out property and will heavily contaminate the spray equipment.

SUMMARY

We found that a crystal form of halosulfuron-methyl, "crystalline modification I", has an improved spray equipment clean-out property and reduces residual halosulfuron-methyl contamination of spray equipment.

We have surprisingly found that combining the crystalline modification I of mesotrione with the crystalline modification I of halosulfuron-methyl provides a composition having a synergistic activity, that is, an increased herbicidal activity, compared with the activity expected from the activity of the two components when applied individually.

Accordingly, in a first aspect, the invention provides a herbicidal composition comprising:

(A) the crystalline modification I of 2-(4-mesyl-2-nitrobenzoyl)cyclohexane-1,3-dione (mesotrione); and (B) the crystalline modification I of methyl 3-chloro-5-(4,6-dimethoxypyrimidin-2-ylcarbamoylsulfamoyl)-1-methylpyrazole-4-carboxylate (halosulfuron-methyl).

The composition of the invention is of particular use for controlling the growth of undesirable plant.

In a second aspect, the invention provides a method of controlling the growth of undesirable plant comprising applying to the plant or to the locus thereof a herbicidally effective amount of the herbicidal composition of the first aspect of the present invention.

In a further aspect, the invention provides the use of the herbicidal composition of the first aspect of the present invention in control of undesirable plant growth at a locus.

The references to the crystalline modifications I and II of mesotrione as used herein, refer to the crystalline modification of mesotrione disclosed in WO2006021743, which is incorporated herein by reference in its entirety for all purposes. The crystal modification I of mesotrione is given by the above document as having the following XRD spectrum, although some peak shifting may be possible:

| Peak Position (2-Theta) | Peak Position (d spacing) |
|---|---|
| 8.52 | 10.34 |
| 17.08 | 5.18 |
| 17.43 | 5.08 |
| 18.74 | 4.73 |
| 19.04 | 4.66 |
| 19.31 | 4.59 |
| 19.52 | 4.54 |
| 21.15 | 4.20 |
| 25.73 | 3.46 |
| 28.66 | 3.11 |

Alternatively, the crystalline modification I mesotrione may have a slightly shifted XRD spectrum:

| Peak Position (2-Theta) | Peak Position (d spacing) |
|---|---|
| 8.44 | 10.47 |
| 17.35 | 5.11 |
| 17.55 | 5.05 |
| 18.67 | 4.75 |
| 18.98 | 4.68 |
| 19.24 | 4.61 |
| 19.45 | 4.56 |
| 21.06 | 4.22 |
| 25.64 | 3.47 |
| 28.55 | 3.13 |

The term "herbicide" as used herein, refers to a compound that controls the growth of plants.

The term "herbicidally effective amount" as used herein, refers to the quantity of such a compound or combination of such compounds that is capable of producing a controlling effect on the growth of plants. The controlling effects include all deviation from the natural development of the target plants, for example killing, retardation of one or more aspects of the development and growth of the plant, leaf burn, albinism, dwarfing and the like.

The term "plants" refers to all physical parts of a plant, including shoots, leaves, needles, stalks, stems, fruit bodies, fruits, seeds, roots, tubers and rhizomes.

The term "locus" refers to the place on which the plants are growing, the place on which the plant propagation materials of the plants are sown or the place on which the plant propagation materials of the plants will be sown.

"At least one" designates a number of the respective compounds or components of 1, 2, 3, 4, 5, 6, 7, 8, 9 or more, preferably 1, 2, or 3.

The synergistic herbicidal composition, the method and use of the present invention are suitable for controlling undesirable plant in a range of crops, including: cereals, for example wheat, barley, rye, oats, corn, rice, sorghum, triticale and related crops; fruit, such as pome fruit, stone fruit and soft fruit, such as apples, pears, plums, peaches, pistachio, almonds, cherries, and berries, for example grape, banana, strawberries, bushberry, caneberry, raspberries and blackberries; leguminous plants, for example beans, lentils, peas, and soybeans; oil plants, for example oilseed rape, mustard and sunflowers; cucurbitaceae, for example cantaloupe, marrows, cucumbers, melons, pumpkin, squash and watermelon; fibrous plants, such as cotton, flax, hemp and jute; citrus fruit, such as oranges, lemons, grapefruit and mandarins; and vegetables, for example spinach, lettuce, asparagus, cabbages, carrots, onions, tomatoes, potatoes, paprika, garlic and leeks; coffee; sugarcane; hops; turf, such as bent grass, buffalo grass, carpet grass, couch, Durban grass, kikuyu grass, perennial ryegrass, Queensland blue couch and tall fescue; tree nuts; as well as ornamentals, for example flowers, such as roses, shrubs, broad-leaved trees and evergreens, such as conifers. Preferably, cereals, fruits, fibrous plants, vegetables, sugarcane and turf. More preferably, corn, rice, sorghum, apple, cotton, tomato, sugarcane and turf.

The control of undesirable plant growth in such crops may be achieved by applying to the locus (A) the crystalline modification I of 2-(4-mesyl-2-nitrobenzoyl)cyclohexane-1, 3-dione (mesotrione) and (B) the crystalline modification I of methyl 3-chloro-5-(4,6-dimethoxypyrimidin-2-ylcarbamoylsulfamoyl)-1-methylpyrazole-4-carboxylate (halosulfuron-methyl) in suitable amounts.

The active compounds (A) and (B) may be applied to the locus together or separately. If applied separately, active compounds (A) and (B) may be applied at the same time and/or consecutively. The control may comprise applying to the plant or the locus thereof a herbicidally effective amount of the herbicidal composition.

BRIEF DESCRIPTION OF DRAWINGS

Various aspects of the invention can be more clearly understood by reference to the drawings, which are described below, and are intended to be illustrative, not limiting, of the invention.

DETAILED DESCRIPTION OF SPECIFIC EMBODIMENTS

Figure 1:
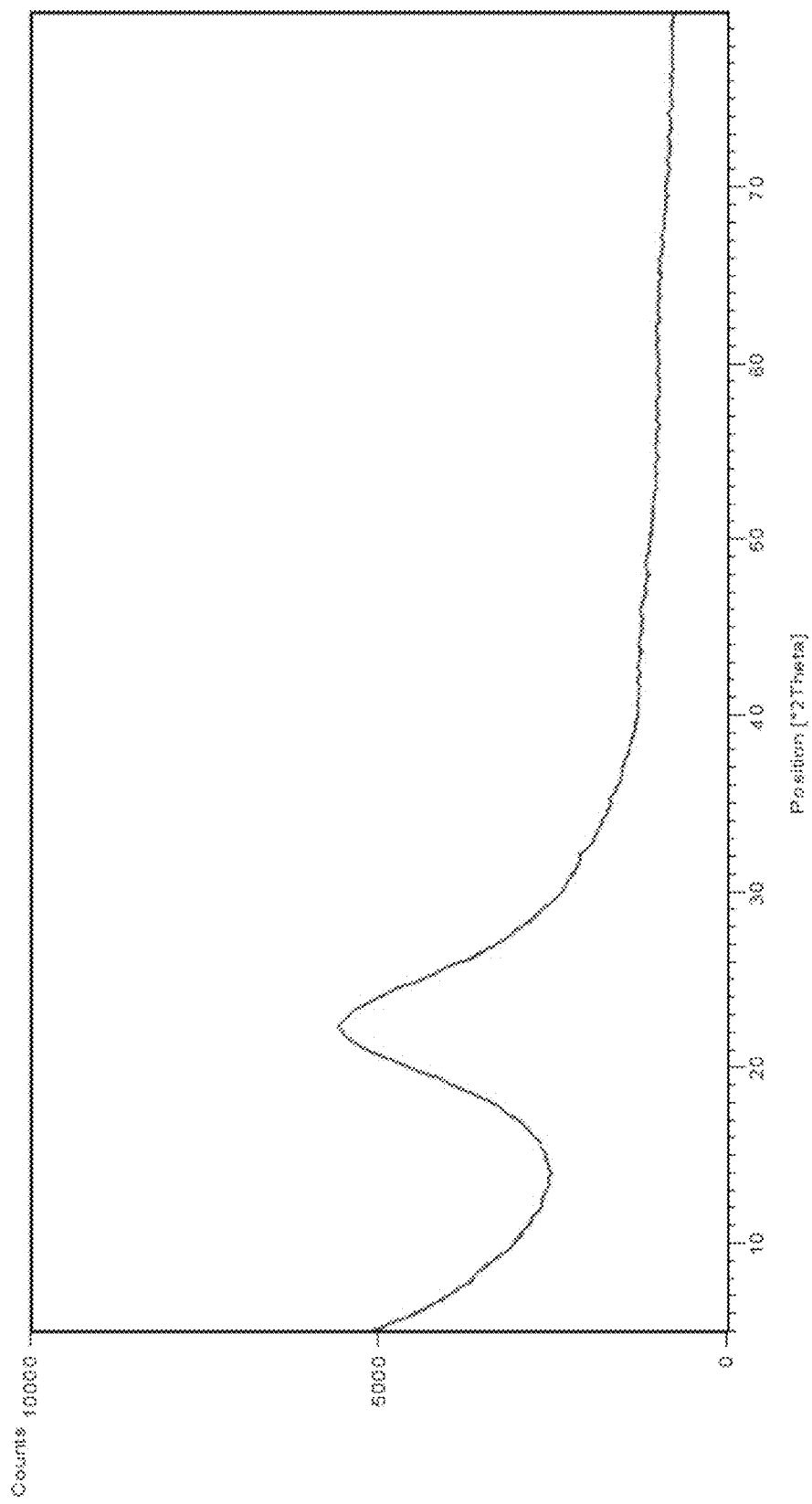
FIG. 1 is a graph showing the results of an X-ray powder diffractogram of amorphous halosulfuron-methyl.

It has been surprisingly found that a combination of (A) the crystalline modification I of 2-(4-mesyl-2-nitrobenzoyl) cyclohexane-1,3-dione (mesotrione) and (B) the crystalline modification I of methyl 3-chloro-5-(4,6-dimethoxypyrimidin-2-ylcarbamoylsulfamoyl)-1-methylpyrazole-4-carboxylate (halosulfuron-methyl) exhibits a synergistic action in the control of many weeds, particularly, but not limit to, perennial weeds, broadleaved weeds, grasses, sedges. For example, weeds that can be controlled by the synergistic composition include one or more of:

African Rue (*Peganum Harmala*), Alkali Mallow (*Malvella leprosa*), Alligatorweed (*Alternantha philoxeroides*), Alsike Clover (*Trifolium hybridum*), Amaranth (*Amaranthus* spp), Annual Broomweed (*Gutierrezia dracunculoides*), annual knawel, annual mercury (*Mercurialis annua*), Annual Pricklepoppy (*Argemone polyanthemos*), Annual Sowthistle (*Sonchus oleraceus*), Antelope Horn (*Asclepias viridis*), Asiatic Hawksbeard (*Youngia japonica*), Balsam Gourd (*Ibervillea lindheimeri*), Balsam-Apple (*Momordica charantia*), Bastard Toadflax (*Comandra umbellata*), Beggarweed (*Desmodium* spp.), Bindweed, Field (*noxious*) (*Convolvulus arvensis*), Bindweed, Hedge (*Convolvulus sepium*), Bindweed, Texas (*Convolvulus equitans*), Birdsfoot Trefoil (*Lotus corniculatus*), Bittercress, Small-flowered (*Cardamine parviflora*), Bitterweed (*Hymenoxys odorata*), Bitterweed, Brown (*Helenium badium*), Black Medic (*Medicago lupulina*), black mustard, Black Nightshade (*Solanum americanum*), Blackfoot Daisy (*Melampodium leucanthum*), Blackseed Plantain (*Plantago rugelii*), Bladderpod (*Lesquerella gracilis*), blue/purple mustard, Bracted Plantain (*Plantago aristata*), broadleaf dock, Broadleaf Plantains (*Plantago* spp.), Buckhorn Plantain (*Plantago lanceolata*), Buffalo Gourd (*Cucurbita foetidissima*), Buffalobur (*Solanum rostratum*), Bulbous Buttercup (*Ranunculus bulbosus*), Bull Thistle (*Cirsium vulgare*), bur buttercup, Bur Clover (*Medicago hispida*), Burcucumber (*Sicyos angulatus*), Bushy Buttonweed (*Spermacoce assurgens*), Bushy Wallflower (*Erysimum repandum*), bushy wallflower, Butterweed (*Senecio glabellus*), Camphorweed (*Heterotheca subaxillaris*), Canada Thistle (*Cirsium arvense*), Carolina False Dandelion (*Pyrrhopappus carolinianus*), Carolina *geranium*, Carpetweed (*Mollugo verticillata*), Catchweed Bedstraw (*Galium aparine*), Centella, Chamberbitter (*Phyllanthus urinaria*), Chicory (*Cichorium intybus*), Cinquefoil, Clammy Groundcherry (*Physalis heterophylla*), clasping pepperwee, Climbing Hempweed (*Mikania scandens*), coast fiddleneck, Coat Buttons (*Tridax procumbens*), Common Beggar-tick (*Bidens alba*), common buckwheat, Common Burdock (*Arctium minus*), Common Chickweed (*Stellaria media*), Common Cocklebur (*Xanthium strumarium*), Common Groundsel (*Senecio vulgaris*), Common Lambsquarters (*Chenopodium album*), Common Mallow, Common Milkweed (*Asclepias syriaca*), Common Mullein (*Verbascum thapsus*), common orache (*Atriplex patula*), Common Pokeweed (*Phytolacca americana*), Common Purslane (*Portulaca oleracea*), common radish, Common Ragweed (*Ambrosia artemisiifolia*), Common Sneezeweed (*Helenium amarum*), Common Sunflower (*Helianthus annuus*), Common Waterhemp (*Amaranthus rudis*), Common Yarrow (*Achillea millefolium*), Compass Plant (*Silphium laciniatum*), conical catchfly, Coreopsis (*Coreopsis tinctoria*), corn chamomile, Corn Gromwell (*Lithospermum arvense*), Corn Speedwell (*Veronica arvensis*), corn spurry, Cowcockle (*Vaccaria pyramidata*), Cowpen Daisy (*Verbesina encelioides*), Creeping Beggarweed (*Desmodium incanum*), creeping buttercup (*Ranunculus repens*), Creeping Cucumber (*Melothria pendula*), Creeping Indigo (*Indigofera spicata*), Creeping *Oxalis*, Creeping Speedwell, Creeping Woodsorrel (*Oxalis corniculata*), cress, *Croton*, Texas (*Croton texensis*), *Croton*, Tropic (*Croton glandulosus*), *Croton*, Woolly (*Croton capitatus*), Cup Plant (*Silphium perfoliatum*), Cupid's Shaving Brush (*Emilia sonchifolia*), Curly Dock (*Rumex crispus*), Curlycup Gumweed (*Grind-* elia squarrosa), Cutleaf Eveningprimose (*Oenothera laciniata*), Cutleaf Groundcherry (*Physalis angulata*), Daisy Fleabane (*Erigeron annuus*), Dakota Verbena (*Verbena bipinnatifida*), Dandelion (*Taraxacum officinale*), Dayflower (*Commelina*), Deadnettle, Purple (*Lamium purpureum*), Devil's Claw (*Proboscidea louisianica*), Dichondra, Dogfennel (*Euphorbia capillifolium*), Elderberry (*Sambucus canadensis*), Englemann Daisy (*Englemannia pinnatifida*), false chamomile, False Daisy or Eclipta (*Eclipta prostrata*), False Nightshade (*Chamaesaracha coronopus*), field chickweed, Field Dodder (*Cuscuta campestris*), field pennycress, Filaree, California or Redstem (*Erodium cicutarium*), Filaree, Texas or Storkbill (*Erodium texanum*), fixweed, Flixweed (*Descurainia sophia*), Florida Pellitory (*Parietaria floridana*), Garden Rocket (*Eruca vesicaria* ssp. *sativa*), Garden Spurge (*Chamaesyce hirta*), Germander (*Teucrium cubense*), Giant Ragweed (*Ambrosia trifida*), Goldenrod (*Solidago* spp.), goosefoots (*Chenopodium* spp.), Gray Tidestrom (*Tidestromia lanuginosa*), great ragweed (*Ambrosia trifida*), Greenbriar (*Smilax* spp.), Greenthread (*Thelesperma filifolium*), Ground Spurge (*Euphorbia prostrata*), groundsel, Hairy Caltrop (*Kallstroemia hirsutissina*), Hairy Nightshade (*Solanum sarrachoides*), Hedge Parsley (*Torilis arvensis*), Hemp Dogbane (*Apocynum cannabinum*), Hemp Sesbania (*Sesbania exaltata*), Henbit (*Lamium amplexicaule*), Hogpotato (*Hoffmanseggia densiflora*), Honeysuckle (*Lonicera* spp.), Hophornbeam Copperleaf (*Acalypha ostryaefolia*), Horehound (*Marrubium vulgare*), Horse purslane (*Trianthema portulacastrum*), Horsenettle (*Solanum carolinense*), Horseweed (*Conyza canadensis*), Huisachedaisy (*Amblyolepis setigera*), Hyssop Spurge (*Chamaesyce hyssopifolia*), Illinois Bundleflower (*Desmanthus illinoensis*), Indian Blanket (*Gaillardia pulchella*), Indian Mallow (*Abutilon incana*), Japanese Hops (*Humulus japonicus*), Jerusalem Artichoke (*Helianthus tuberosus*), Jimsonweed (*Datura stramonium*), Khakiweed (*Alternanthera pungens*), knotweed (*polygonum* spp.), Kochia (*Kochia scoparia*), Kudzu (noxious) (*Pueraria lobata*), Lamb's-qamaranthusuarters (*Chenopodium album*), Lanceleaf Sage (*Salvania reflexa*), Lantana (*Lantana camara*), Livid Amaranth (*Amaranthus blitum*), Lizardtail Gaura (*Gaura Parviflora*), London rocket, Long Fruited Primrose-Willow (*Ludwigia octovalvis*), Marijuana (noxious) (*Cannabis sativa*), Marsh Parsley (*Cyclospermum leptophylum*), marshelder, Match-Head (*Phyla nodiflora*), mayweed chamomile, Mexicanhat (*Ratibida columnaris*), Mexican-Poppy (*Argemone mexicana*), miners lettuce, Mock Bishop's Weed (*Ptilimnium capillaceum*), Morningglory, Bigroot (*Ipomoea pandurata*), Morningglory, Ivyleaf (*Ipomoea hederacea*), Morningglory, Pitted (*Ipomoea lacunosa*), Morningglory, Sharppod (*Ipomoea trichocarpa*), Morningglory, Tall (*Ipomoea purpurea*), Mouseear Chickweed (*Cerastium vulgatum*), Mousetail (*Myosurus minimus*), Multiflora rose (noxious) (*Rosa multiflora*), Mustard, London Rocket (*Sisymbrium irio*), Mustard, Pinnatetansy (*Descurainia pinnate*), Mustard, Tansy (*Descurainia pinnata*), Mustard, Tumble (*Sisymbrium altissimum*), Mustard, Turnip Weed (*Rapistrum rugosum*), Mustard, Wild (*Brassica kaber*), narrowleaf lambsquarters, ightflowering catchfly, Nodding Spurge (*Euphorbia nutans*), Orange Globe Mallow (*Sphaeralcea occidentalis*), Oxeye Daisy (*Chrysanthemum leucanthemum*), Palmer Amaranth (*Amaranthus palmeri*), Partridgepea (*Cassia chamaecrista*), Pennsylvania smartweed, Pennycress, Field (*Thlaspi arvense*), pigweed, Pigweed, Prostrate (*Amaranthus blitoides*), Pigweed, Redroot (*Amaranthus retroflexus*), Pigweed, Tumble (*Amaranthus albus*), pineappleweed, plains coreopsis, Poison Hemlock (*Conium maculatum*), prickly lettuce, Prickly Pear (*Opuntia* spp.), Prickly Sida (*Sida spinosa*), Prostrate Knotweed (*Polygonum aviculare*), Puncturevine (*Tribulus terrestris*), Purple Flower Groundcherry (*Physalis lobata*), Purple Horsemint (*Monarda citriodora*), Purple Loosestrife (noxious) (*Lythrum salicaria*), Purslane Speedwell (*Veronica peregrina*), Rain Lily (*Cooperia drummondii*), Rattlesnake master (*Eryngium yuccifolium*), Red Hornedpoppy (*Glaucium corniculatum*), redmaids, redroot pigweed (*Amaranthus retroflexus*), Riddell Groundsel (*Senecio riddellii*), Rosinweed (*Silphium integrifolium*), rough cocklebur (*Xanthium strumarium*), Russian thistle, Saltmarsh Fleabane (*Pluchea odorata*), Santa Maria or *Parthenium* Pancake Weed (*Parthenium hysterophorus*), Sawtooth aster (*Prionopsis ciliata*), Scarlet Gaura (*Gaura coccinea*), Scarlet Musk Flower (*Nyctaginia capitata*), scentless chamomile, Scrambledeggs (*Corydalis curvisiliqua*), Shepherd's Purse (*Capsella bursa-pastoris*), Sicklepod (*Senna obtusifolia*), SilverLeaf Cassia (*Cassia phyllodinea*), Silverleaf Nightshade (*Solanum elaeagnifolium*), Silversage (*Artemesia ludoviciana*), Silversheath Knotweed (*Polygonum argyrocoleon*), Skeletonweed (*Lygodesmia juncea*), Slender Aster (*Aster gracilis*), smallflower buttercup, Smallhead Sneezeweed (*Helenium microcephalum*), Smallseed Falseflax (*Camelina microcarpa*), smartweed, Smartweed, Pale (*Polygonum lapathifolium*), Smartweed, Pennsylvania (*Polygonum pensylvanicum*), Smooth Groundcherry (*Physalis subglabrata*), Smooth Sumac (*Rhus glabra*), snow speedwede, Snow-on-the-mountain (*Euphorbia marginata*), Southern Sida (*Sida acuta*), Spiny Pigweed (*Amaranthus spinosus*), Spiny Sowthistle (*Sonchus asper*), Sprawling Horseweed (*Calyptocarpus vialis*), Spreading Dayflower (*Commelina diffusa*), Spurge, Leafy (*Euphorbia esula*), Spurge, Prostrate (*Euphorbia humistrata*), Spurge, Toothed (*Euphorbia dentata*), Spurred Anoda (*Anoda cristata*), sticky chickweed, stinking mayweed/dogfennel, Sweet-potato (*Ipomea batatas*), swinecress, Tahoka Daisy (*Machaeranthera tanacetifolia*), tansymustard, tarweed fiddleneck, Texas Blueweed (*Helianthus ciliaris*), Texas Bullnettle (*Cnidoscolus texanus*), Thistle, Blessed Milk (*Silybum marianum*), Thistle, Distaff (*Carthamus lanatus*), Thistle, Malta Star (*Centaurea melitensis*), Thistle, Musk (noxious) (*Carduus nutans*), Thistle, Scotch (noxious) (*Onopordum acanthium*), Thistle, Tall (*Cirsium altissimum*), Thistle, Texas Purple (*Cirsium texanum*), Threadleaf Groundsel (*Senecio longilobus*), Toothcup (*Ammannia latifolia*), Trumpetcreeper (*Campsis radicans*), tumble, Twinleaf Sennia (*Senna roemeriana*), Velvetleaf (*Abutilon theophrasti*), Venice Mallow (*Hibiscus trionum*), Vetch (*Vicia* spp.), Virginia Copperleaf (*Acalypha virginica*), Virginia Creeper (*Parthenocissus quinquefolia*), Virginia Pepperweed (*Lepidium virginicum*), volunteer adzuki bean (*Vigna angularis*), volunteer lentils, volunteer peas, volunteer sunflower, Wandering Cudweed (*Gnaphalium pensylvanicum*), Waterhemlock (*Cicuta maculata*), Waterhemp (*Amaranthus tuberculatus*), Waterleaf (*Nama hispidum*), waterpod, Western Ragweed (*Ambrosia psilostachya*), Western Salsify (*Tragopogon dubuis*), White Foxglove Beardtongue (*Penstemon digitalis*), White Heath Aster (*Aster pilosus*), White Snakeroot (*Eupatorium rugosum*), Wild Buckwheat (*Polygonum convolvulus*), Wild Carrot (*Daucus carota*), wild chamomile, wild garlic, Wild *Geranium* (*Geranium carolinanum*), Wild Lettuce (*Lactuca serriola*), wild mustard (*Sinapis arvensis*), wild radish, Woollyleaf Bursage (*Ambrosia grayi*), Woollywhite, Chalkhill (*Hymenopappus tenuifolius*), Woollywhite, Yellow (*Hymenopappus flavescens*), Wright Eryngo (*Eryngium heterophyllum*), Yellow Rocket (*Barbarea vulgaris*), Yellow Sweetclover (*Melilotus*

*indica*), Nightshade, Eastern black (*Solanum ptycanthum*), Cockspur (*Echinochola crusgalli*), Large crabgrass (*Digitaria sanginalis*), (*Septaria viridis*), Wild foxtail millet (*Setaria viridis*), *Acalypha australis*, Mullumbumby couch (*Cyperus brevifolus*), Nutgrass (*Cyperus rotundus*), Annual kyllinga (*Kyllinga sesquiflorus*), Bindweed, hedge (*Calystegia sepium*), Bog bulrush (*Schoenoplectus mucronatus*), California arrowhead (*Sagittaria montevidensis*), Corn spurry (*Spergula arvensis*), Devils Claw (*Probiscidea louisiana*), False daisy (*Ecilpta prostrata*), Fleabane Philadelphia (*Erigeron philadelphicus*), Galinsoga, hairy (*Galinsoga quadriradiata*), Green *kyllinga* (*Kyllinga breviflora*), Horsetail (*Equisetum arvense*), Horseweed (*Erigeron canadensis*), Ladysthumb (*Polygonum persicaria*), Mallow (*Malva neglecta*), Milkweed, honeyvine (*Cyanchum leave*), Nutsedge, yellow (*Cyperus esculentus*), Pigweed, smooth (*Amaranthus hybridus*), Radish, wild (*Raphanus raphanistrum*), Sea clubrush (*Bolboschoenus maritimus*), Shepherdspurse (*Capsella bursapastoris*), Stinking chamomile (*Anthemis cotula*), Willowherb, fringed (*Epilobium ciliatum*), Yellowcress, creeping (*Rorippa sylvestris*), (*Cyperus* spp., *Alisma* spp.

Preferably, the weeds to be controlled include one or more of *Abutilon* spp., *Amaranthus* spp., *Ambrosia* spp., *Bolboschoenus* spp., *Chenopodium* spp., *Cyperus* spp., *Echinochola* spp., *Equisetum* spp., *Ipomoea* spp., *Kyllinga* spp., *Lamium* spp., *Sinapis* spp., *Stellaria* spp.

More preferably, the weeds to be controlled include one or more of Annual *kyllinga* (*Kyllinga sesquiflorus*), Chickweed (*Stellaria media*), Cockspur (*Echinochola crusgalli*), Deadnettle, purple (*Lamium purpureum*), Horsetail (*Equisetum arvense*), Lambsquarters, common (*Chenopodium album*), Morningglory, ivyleaf (*Ipomoea hederacea*), Mullumbimby Couch (*Cyperus brevifolus*), Mustard, wild (*Sinapis arvensis*), Nutgrass (*Cyperus rotundus*), Nutsedge, yellow (*Cyperus esculentus*), Pigweed, Redroot (*Amaranthus retroflexus*), Pigweed, smooth (*Amaranthus hybridus*), Ragweed, common (*Ambrosia artemisiifolia*), Sea clubrush (*Bolboschoenus maritimus*), Velvetleaf (*Abutilon theophrasti*).

The crystal modification I of halosulfuron-methyl has an XRD spectrum that includes at least 3 of the following reflexes as 2θ values in an X-ray powder diffractogram recorded using Cu-Kα radiation at 25° C.:

$$2\theta=8.80\pm0.2 \quad (1)$$

$$2\theta=13.48\pm0.2 \quad (2)$$

$$2\theta=13.72\pm0.2 \quad (3)$$

$$2\theta=16.20\pm0.2 \quad (4)$$

$$2\theta=17.71\pm0.2 \quad (5)$$

$$2\theta=18.61\pm0.2 \quad (6)$$

$$2\theta=20.48\pm0.2 \quad (7)$$

$$2\theta=21.38\pm0.2 \quad (8)$$

$$2\theta=22.60\pm0.2 \quad (9)$$

$$2\theta=24.71\pm0.2 \quad (10)$$

$$2\theta=25.53\pm0.2 \quad (11)$$

$$2\theta=25.83\pm0.2 \quad (12)$$

$$2\theta=26.53\pm0.2 \quad (13)$$

$$2\theta=26.72\pm0.2 \quad (14)$$

Figure 4:
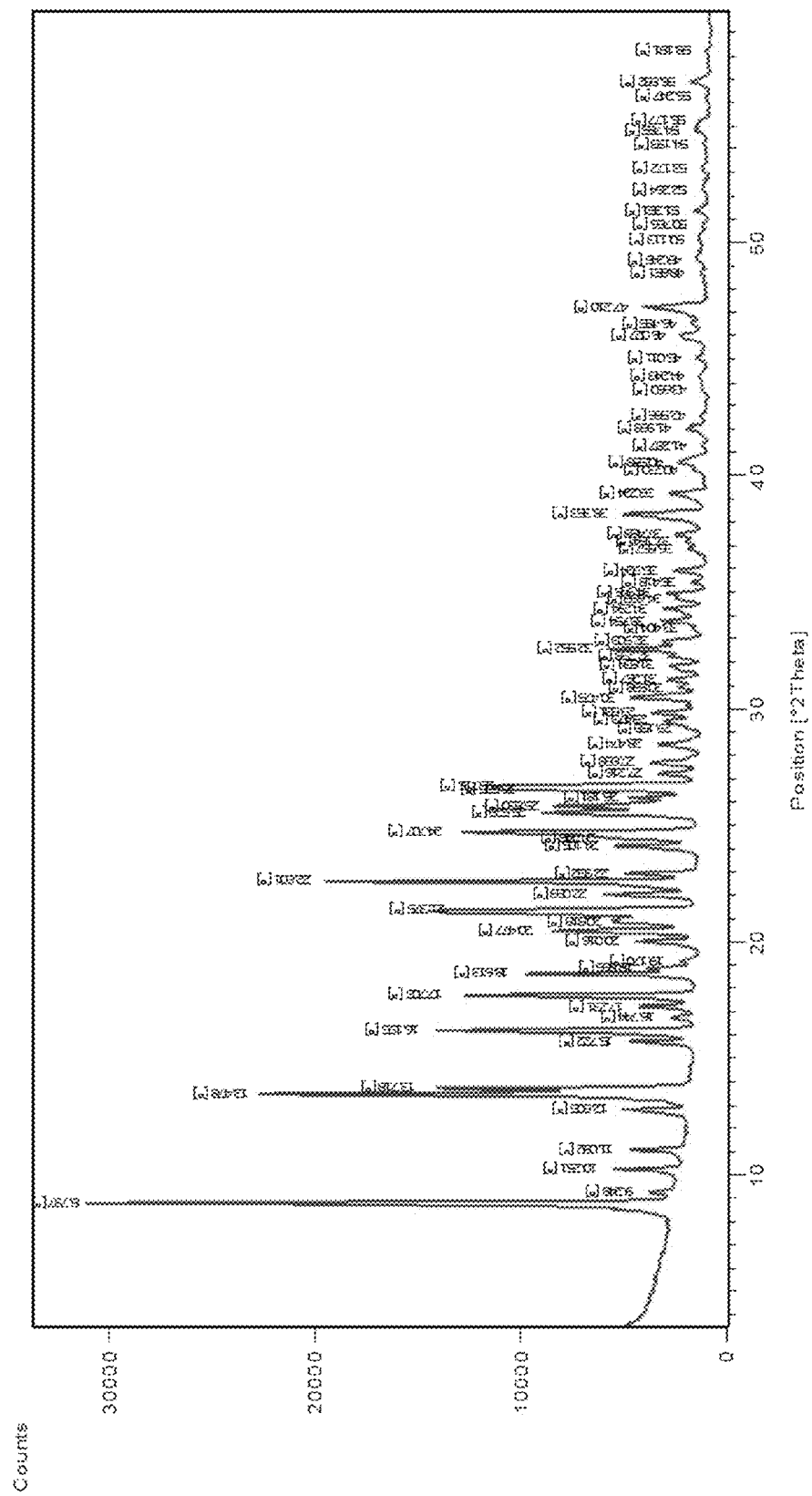
FIG. 4 is a graph showing the results of an X-ray powder diffractogram (XRD) of crystalline modification I of halosulfuron-methyl, according to an embodiment of the invention.

The crystalline modification I of halosulfuron-methyl of the invention is characterized by an X-ray powder diffractogram having at least three of the reflexes indicated above. Preferably, the crystalline modification I is one having at least four of the aforementioned reflexes, more preferably at least five, six, or seven, or eight of said reflexes. An X-ray powder diffractogram of the crystalline modification I of halosulfuron-methyl is shown in FIG. 4.

According to a preferred embodiment the crystalline modification I of halosulfuron-methyl exhibits at least 3, 4, or 5 or all of the reflexes from the following:

$$2\theta=8.80\pm0.2 \quad (1)$$

$$2\theta=13.48\pm0.2 \quad (2)$$

$$2\theta=13.72\pm0.2 \quad (3)$$

$$2\theta=16.20\pm0.2 \quad (4)$$

$$2\theta=17.71\pm0.2 \quad (5)$$

$$2\theta=21.38\pm0.2 \quad (8)$$

$$2\theta=22.60\pm0.2 \quad (9)$$

$$2\theta=24.71\pm0.2 \quad (10)$$

$$2\theta=26.72\pm0.2 \quad (14)$$

The crystalline modification I of halosulfuron-methyl may be further characterized by Infrared (IR) spectroscopy. The IR spectrum was measured with the resolution of 4 $cm^{-1}$ and with the number of scans of 16 for the purified sample. The IR spectrum of crystalline modification I of halosulfuron-methyl can be identified by its characteristic functional group vibrations at 3248.48, 2160.45, 2032.49, 1726.30, 1708.12 and 1608.81 $cm^{-1}$ as shown in FIG. 3.

All IR spectra were obtained using the following acquisition parameters:

| FT-IR spectrometer | Bruker Tensor 37 |
| --- | --- |
| Diamond ATR unit | from Specac |
| Wavelength range | 550-4000 $cm^{-1}$ |
| Resolution | 4 $cm^{-1}$ |
| Number of scans | 16 |

Figure 3:
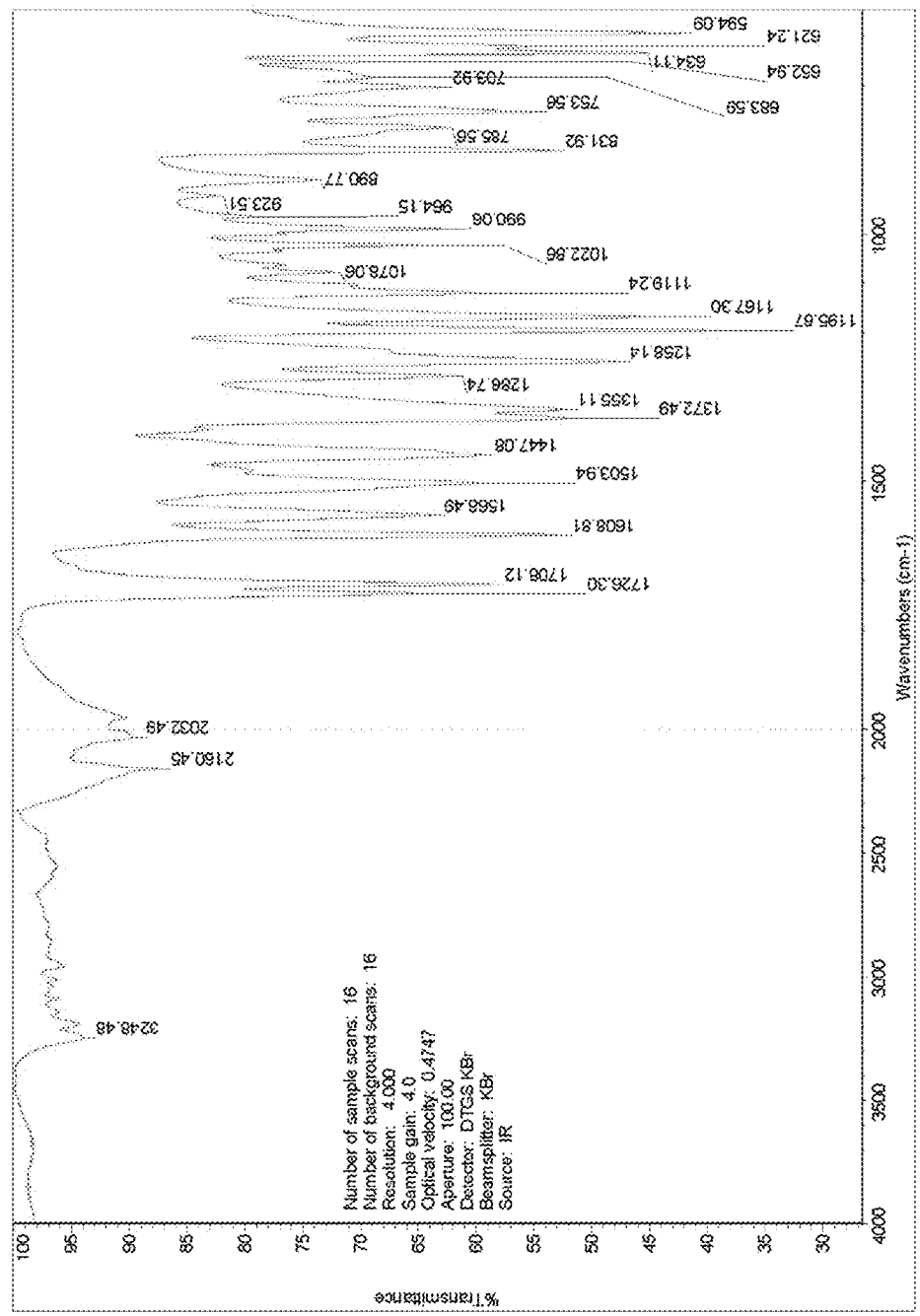
FIG. 3 is a graph showing the results of an infrared (IR) spectrograph of crystalline modification I of halosulfuron-methyl, according to an embodiment of the invention.

The crystalline modification I of halosulfuron-methyl according to an embodiment of the invention may be further characterized by Differential Scanning Calorimetry (DSC) (FIG. 3). An endothermic peak with onset at about 176.1° C. and peak maximum at about 178.4° C. is shown in FIG. 1.

Methods of making the crystalline modification I of halosulfuron-methyl are described in copending U.S. Ser. No. 14/955,385, filed on even date herewith, the entire contents of which are incorporated herein by reference for all purposes. More particularly, methods for preparing amorphous halosulfuron-methyl are well known in the art. Amorphous halosulfuron-methyl is manufactured and available on a commercial scale. A particularly suitable method for preparing amorphous halosulfuron-methyl is described in U.S. Pat. No. 4,668,277 the entire contents of which are incorporated herein by reference for all purposes.

According to an embodiment of the invention, the crystalline modification I of halosulfuron-methyl can be obtained by the processes below:

Halosulfuron-methyl in amorphous state is dissolved and then crystallized from solvents.

In one aspect, the invention provides a process for preparing a crystalline modification I of halosulfuron-methyl comprising steps of:
i) dissolution of amorphous halosulfuron-methyl into a solvent;
ii) precipitation of the dissolved compound into crystalline modification I of halosulfuron-methyl of formula I; and
iii) isolation of the precipitated crystalline modification I.

Suitable solvents for preparing crystalline modification I of halosulfuron-methyl include halogenated hydrocarbons (for example, trifluoro methyl benzene, chlorobenzene, bromobenzene, dichlorobenzene, chlorotoluene and trichlorobenzene), ethers (for example, ethyl propyl ether, n-butyl ether, anisole, phenetole, cyclohexyl methyl ether, dimethyl ether, diethyl ether, dimethyl glycol, diphenyl ether, dipropyl ether, diisopropyl ether, di-n-butyl ether, diisobutyl ether, diisoamyl ether, ethylene glycol dimethyl ether, isopropyl ethyl ether, methyl tert-butyl ether, tetrahydrofuran, methyltetrahydrofuran, dioxane, dichlorodiethyl ether, methyltetrahydrofuran, polyethers of ethylene oxide and/or propylene oxide), nitrated hydrocarbons (for example, nitromethane, nitroethane, nitropropane, nitrobenzene, chloronitrobenzene and o-nitrotoluene), aliphatic, cycloaliphatic or aromatic hydrocarbons (for example, pentane, n-hexane, n-heptane, n-octane, nonane, ethyl benzene, mesitylene), cymene, petroleum fractions within a boiling range of from 70° C. to 190° C., (cyclohexane, methylcyclohexane, petroleum ether, ligroin, octane, benzene, toluene and xylene), esters (for example, malonates, acetic acid n-butyl ester (n-butyl acetate), methyl acetate, ethyl acetate, isobutyl acetate, dimethyl carbonate, diethyl carbonate, dibutyl carbonate and ethylene carbonate), methyl ethyl ketone and aliphatic alcohols (for example, methanol, isopropyl alcohol, ethanol, n-propanol, isopropanol, n-butanol and tert-amyl alcohol).

Preferred solvents are nitrobenzene, toluene, xylene, benzene, chlorobenzene, dichlorobenzene, ethyl benzene, trifluoro methyl benzene, mesitylene, ether, methyl ethyl ketone.

In the present invention, it is preferred that the solvent comprises methyl ethyl ketone and/or xylene.

Hence, according to a preferred embodiment in step (i), amorphous halosulfuron-methyl is dissolved in a solvent comprising methyl ethyl ketone and/or xylene.

The total amount of (A) and (B) is from 5% to 99% by weight of the composition. The crystalline modification I of mesotrione may be present in the synergistic herbicidal composition of an embodiment of the invention in any suitable amount, and is generally present in an amount of from about 1% to about 90% by weight of the composition, preferably from about 1% to about 80% by weight, more preferably from about 1% to about 70% by weight of the composition, most preferably from about 10% to about 60%. The crystalline modification I of halosulfuron-methyl may be present in the synergistic herbicidal composition in any suitable amount, and is generally present in an amount of from about 1% to about 90% by weight of the composition, preferably from about 1% to about 80% by weight, more preferably from about 1% to about 70% by weight of the composition, most preferably from about 1% to about 40%.

(A) and (B) may be employed in the composition, method or use of an embodiment of the invention in any suitable weight ratio. The weight ratio of the crystalline modification I of mesotrione and the crystalline modification I of halosulfuron-methyl in the composition may be in the range of from about 99:1 to about 1:99, preferably from about 90:1 to about 1:90, more preferably from about 80:1 to about 1:80, still more preferably from about 70:1 to about 1:70, more preferably still from about 50:1 to about 1:50, 40:1 to about 1:40, about 40:1 to about 1:15, about 30:1 to about 1:10, about 20:1 to 1:5.

In general, the application rate of the active ingredients depends on such factors as the type of weed, type of crop plant, soil type, season, climate, soil ecology and various other factors. The application rate of the composition for a given set of conditions can readily be determined by routine trials.

In general the composition or the method of an embodiment of the invention can be applied at an application rate of from about 0.005 kilograms/hectare (kg/ha) to about 5.0 kg/ha of the total amount of active ingredient (A) and (B) being applied. Preferably, the application rate is from about 0.01 kg/ha to about 3.0 kg/ha of the active ingredients.

Preferably, the application rate of the active ingredients is from 1 to 1000 g/ha of (A) the crystalline modification I of mesotrione and from 1 to 500 g/ha of (B) the crystalline modification I of halosulfuron-methyl. More preferably, the application rate of the active ingredients is from 1 to 500 g/ha of (A) the crystalline modification I of mesotrione and from 5 to 200 g/ha of (B) the crystalline modification I of halosulfuron-methyl. More preferably, the application rate of the active ingredients is from 1 to 400 g/ha of (A) the crystalline modification I of mesotrione and from 10 to 150 g/ha of (B) the crystalline modification I of halosulfuron-methyl.

As noted above, in an embodiment of the invention, (A) the crystalline modification I of mesotrione and (B) the crystalline modification I of halosulfuron-methyl may be applied either separately or combined as part of a two-part herbicidal system, such as the composition of the present invention. The composition is applied pre-planting, pre-emergence and/or post-emergence.

The compositions of embodiments of this invention can be formulated in conventional manner, for example by mixing (A) the crystalline modification I of mesotrione and (B) the crystalline modification I of halosulfuron-methyl with appropriate auxiliaries. Suitable auxiliaries will depend upon such factors as the type of formulation and will be known to the person skilled in the art.

In particular, the composition may further comprise one or more auxiliaries selected from extenders, carriers, solvents, surfactants, stabilizers, anti-foaming agents, anti-freezing agents, preservatives, antioxidants, colorants, thickening agents, solid adherents, fillers, wetting agents, dispersing agents, lubricants, anticaking agents and diluents. Such auxiliaries are known in the art and are commercially available. Their use in the formulation of the compositions of the present invention will be apparent to the person skilled in the art.

Suitable formulations for applying a combination of (A) and (B) include water-soluble concentrates (SL), emulsifiable concentrates (EC), emulsions (EW), micro-emulsions (ME), suspension concentrates (SC), oil-based suspension concentrates (OD), flowable suspensions (FS), water-dispersible granules (WG), water-soluble granules (SG), wettable powders (WP), water soluble powders (SP), granules (GR), encapsulated granules (CG), fine granules (FG), macrogranules (GG), aqueous suspo-emulsions (SE), capsule suspensions (CS) and microgranules (MG). Preferred formulations are suspension concentrates (SC), water-dispersible granules (WG) and wettable powders (WP).

The composition may comprise one or more inert fillers. Such inert fillers are known in the art and available commercially. Suitable fillers include, for example, natural ground minerals, such as kaolins, aluminas, talc, chalk, quartz, attapulgite, montmorillonite, and diatomaceous earth, or synthetic ground minerals, such as highly dispersed silicic acid, aluminum oxide, silicates, and calcium phosphates and calcium hydrogen phosphates. Suitable inert fillers for granules include, for example, crushed and fractionated natural minerals, such as calcite, marble, pumice, sepiolite, and dolomite, or synthetic granules of inorganic and organic ground materials, as well as granules of organic material, such as sawdust, coconut husks, corn cobs, and tobacco stalks.

The composition may optionally include one or more surfactants which are preferably non-ionic, cationic and/or anionic in nature and surfactant mixtures which have good emulsifying, dispersing and wetting properties, depending upon the active compound/compounds being formulated. Suitable surfactants are known in the art and are commercially available.

Suitable anionic surfactants can be both so-called water-soluble soaps and water-soluble synthetic surface-active compounds. Soaps which may be used include the alkali metal, alkaline earth metal or substituted or unsubstituted ammonium salts of higher fatty acid ($C_{10}$ to $C_{22}$), for example the sodium or potassium salt of oleic or stearic acid, or of natural fatty acid mixtures.

The surfactant may comprise an emulsifier, dispersant or wetting agent of ionic or nonionic type. Examples of such agents include salts of polyacrylic acids, salts of lignosulphonic acid, salts of phenylsulphonic or naphthalenesulphonic acids, polycondensates of ethylene oxide with fatty alcohols or with fatty acids or with fatty amines, substituted phenols, especially alkylphenols, sulphosuccinic ester salts, taurine derivatives, especially alkyltaurates, and phosphoric esters of polyethoxylated phenols or alcohols.

The presence of at least one surfactant is generally required when the active compound and/or the inert carrier and/or auxiliary/adjuvant are insoluble in water and the vehicle for the final application of the composition is water.

The composition may optionally further comprise one or more polymeric stabilizers. Suitable polymeric stabilizers that may be used in the present invention include, but are not limited to, polypropylene, polyisobutylene, polyisoprene, copolymers of monoolefins and diolefins, polyacrylates, polystyrene, polyvinyl acetate, polyurethanes or polyamides. Suitable stabilizers are known in the art and commercially available.

The surfactants and polymeric stabilizers mentioned above are generally believed to impart stability to the composition, in turn allowing the composition to be formulated, stored, transported and applied.

Suitable anti-foaming agents for use in the compositions include all substances which can normally be used for this purpose in agrochemical compositions. Suitable anti-foaming agents are known in the art and are available commercially. Particularly preferred antifoam agents are mixtures of polydimethylsiloxanes and perfluroalkylphosphonic acids, such as the silicone anti-foaming agents available from GE or Compton.

Suitable solvents for use in the compositions may be selected from all customary organic solvents which thoroughly dissolve the active compounds employed. Again, suitable organic solvents for (A) and (B) are known in the art. The following may be mentioned as being preferred: N-methyl pyrrolidone, N-octyl pyrrolidone, cyclohexyl-1-pyrrolidone; and a mixture of paraffinic, isoparaffinic, cycloparaffinic and aromatic hydrocarbons (available commercially as SOLVESSO™200). Suitable solvents are commercially available.

Suitable preservatives include all substances which can normally be used for this purpose in agrochemical compositions of this type and again are well known in the art. Suitable examples that may be mentioned include PREVENTOL® (from Bayer AG) and PROXEL® (from Bayer AG).

The compositions may comprise an antioxidant. Suitable antioxidants are all substances which can normally be used for this purpose in agrochemical compositions, as is known in the art. Preference is given to butylated hydroxytoluene.

Suitable thickening agents for use in the compositions include all substances which can normally be used for this purpose in agrochemical compositions. Examples include xanthan gum, PVOH, cellulose and its derivatives, clay hydrated silicates, magnesium aluminum silicates or a mixture thereof. Again, such thickening agents are known in the art and available commercially.

The compositions may further comprise one or more solid adherents. Such adherents are known in the art and available commercially. They include organic adhesives, including tackifiers, such as celluloses of substituted celluloses, natural and synthetic polymers in the form of powders, granules, or lattices, and inorganic adhesives such as gypsum, silica, or cement.

In addition, depending upon the formulation, the composition according to the invention may also comprise water.

The formulated composition may for example be applied in spray form, for example employing appropriate dilutions using a diluent, such as water.

In the method and use of an embodiment of the invention, the combination of the active ingredients can be applied to the locus where control is desired, such as to the leaves of plants and/or the surrounding soil, by a convenient method. The "locus" refers to the place where the plants are growing, the place where the plant propagation materials of the plants are sown or the place where the plant propagation materials of the plants will be sown.

In the event, (A) and (B) are applied simultaneously in an embodiment of the invention, they may be applied as a composition containing (A) and (B), in which case (A) and (B) can be obtained from a separate formulation source and mixed together (known as a tank-mix, ready-to-apply, spray broth, or slurry), optionally with other pesticides, or (A) and (B) can be obtained as a single formulation mixture source (known as a pre-mix, concentrate, formulated compound (or product)), and optionally mixed together with other pesticides.

In a preferred embodiment, the method and use of the present invention employ a composition according to the present invention.

The compositions according to the invention are distinguished by the fact that they are especially well tolerated by crop plants being treated and are environmentally friendly.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined by the appended claims.

Embodiments of the present invention will now be described, for illustrative purposes only, by way of the following examples.

EXAMPLES

Example 1—Preparation of the Crystalline Modification I Mesotrione

The crystalline I modification of mesotrione was prepared according to the method as mentioned in WO2006021743.

Mesotrione enolate suspension was filtered to remove any excess solid enolate. 50 mL of the filtered solution was placed in a reaction flask and heated to 40° C. pH of the solution was adjusted to 2.8 by adding 10% HCl over 20 minutes. Crystals were allowed to stir for 20 minutes before isolated by filtration. The crystals were then washed with water and sucked dry on the filter.

Example 2—Preparation of the Crystalline Modification II Mesotrione

The crystalline II modification of mesotrione was prepared according to the method as mentioned in WO2006021743.

Mesotrione crystals were stirred with water in a reaction flask. pH was increased to 12 by adding NaOH. 1.5 mL of 10% HCl was added over 15 minutes to reduce the pH of the solution to pH 4. Crystals were obtained.

Example 3—Preparation of Amorphous Halosulfuron-Methyl

Halosulfuron-methyl in an amorphous form was prepared according to a method mentioned in U.S. Pat. No. 4,668,277 with modification.

To a mixture of 3-chloro-4-methoxycarbonyl-1-methyl-pyrazole-5-sulfonamide (7.0 g), 5.3 g anhydrous potassium carbonate and 50 ml of dry acetone, 2.8 g of n-butyl isocyanate was added at room temperature. The mixture was refluxed for 3 hours.

After refluxing, acetone was evaporated under reduced pressure and the residue was dissolved in ice-water. After separation of a trace of water insolubles, the filtrate was acidified with hydrochloric acid and the crystals formed were filtered, washed with water and dried to obtain 5.2 g N-(n-butylcarbamoyl)-3-chloro-4-methoxycarbonyl-1-methylpyrazole-5-sulfonamide.

To a mixture of 120 mL of dry toluene and the product obtained from the above procedure, 4.2 g of phosgene was passed under reflux. Then, the reaction mixture was further refluxed for 1.5 hours. After refluxing, solvent was evaporated under reduced pressure to obtain crude 3-chloro-4-ethoxycarbonyl-1-methylpyrazole-5-sulfonyl isocyanate.

The crude isocyanate (0.98 g) was added into 20 mL dry acetonitrile solution having 2-amino-4,6-dimethoxypyrimidine (400 mg). The mixture was stirred at room temperature and the crystals precipitated were filtered, washed and dried to obtain 0.8 g of methyl 3-chloro-5-(4,6-dimethoxypyrimidin-2-ylcarbamoylsulfamoyl)-1-methylpyrazole-4-carboxylate.

As shown in FIG. 1, there is no significant signal from the X-ray powder diffraction pattern. The result indicates the product prepared is amorphous.

Example 4—Preparation of the Crystalline Modification I Halosulfuron-Methyl

Figure 2:
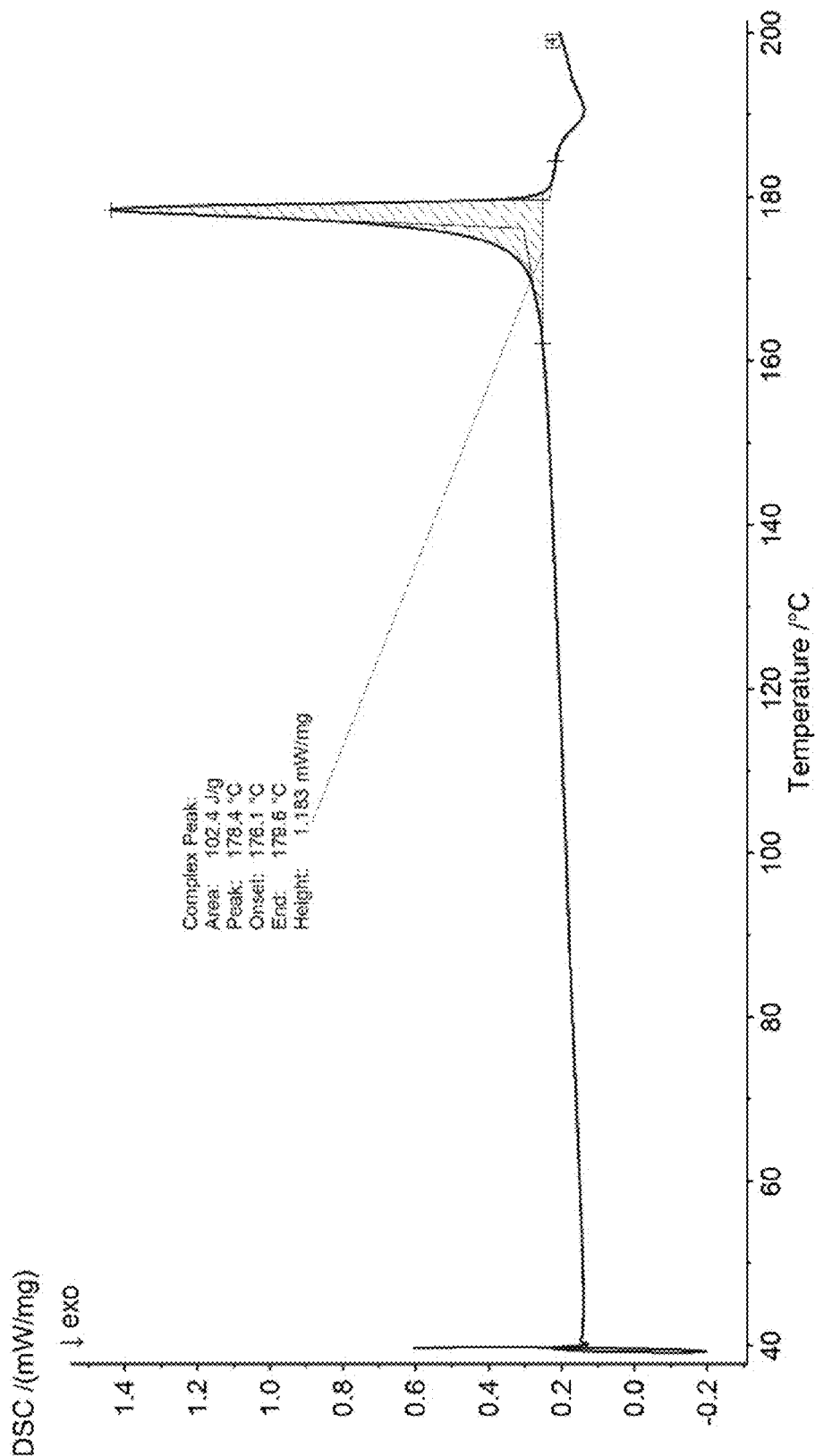
FIG. 2 is a Differential Scanning calorimetry (DSC) thermogram of crystal modification I of halosulfuron-methyl, according to an embodiment of the invention.

Halosulfuron-methyl sample prepared in Example 3 (10 g) was added into a 3 necked round bottom flask along with xylene (60 mL) and the resulting slurry was heated to 90° C. to obtain a homogeneous solution. The insoluble particles, if any, were filtered and the solution was slowly cooled to room temperature. Upon cooling, fine crystals were formed and the heterogeneous mixture was stirred at room temperature for 2 hours. Then, the slurry was filtered and washed with xylene (3 mL). The filtered crystals were dried under vacuum at 60° C. in order to remove the trace xylene from the crystalline product. The crystalline product obtained was having a purity of >98% and the recovered product as crystal was found to be not less than 80% yield. The obtained crystal was analyzed by DSC, IR and X-ray powder diffraction. The results are shown in FIGS. 2, 3, 4 respectively.

Formulation examples Water-dispersible granule (WG) was prepared by mixing and milling of active ingredients and auxiliaries (0.5% SUPRALATE® (sodium lauryl sulfate, Witco Inc., Greenwich), 5% REAX®88B (sodium lignosulfonate, Westvaco Corp), Potassium carbonate (balance to 100%)) under compressed air, then wetting, extruding and drying to obtain water-dispersible granule.

For example,
The crystalline modification I of mesotrione 48%
The crystalline modification I of halosulfuron-methyl 12%
SUPRALATE® (sodium lauryl sulfate, Witco Inc., Greenwich) 0.5%
REAX®88B (sodium lignosulfonate, Westvaco Corp) 5%
Potassium carbonate Balance to 100%

Aqueous suspension concentrates (SC) were prepared by mixing finely ground active ingredients with auxiliaries (10% Propylene glycol, 5% Tristyrylphenol ethoxylates, 1% Sodium lignosulfonate, 1% Carboxymethylcellulose, 1% Silicone oil (in the form of a 75% emulsion in water), 0.1% Xanthan gum, 0.1% NIPACIDE BIT 20, Water (Balance to 1 L).

For example,
The crystalline modification I of mesotrione 30%
The crystalline modification I of halosulfuron-methyl 19.5%
Propylene glycol 10%
Tristyrylphenol ethoxylates 5%
Sodium lignosulfonate 1%
Carboxymethylcellulose 1%
Silicone oil (in the form of a 75% emulsion in water) 1%
Xanthan gum 0.1%
NIPACIDE BIT 20 0.1%
Water Balance to 1 L Wettable powder (WP) was prepared by mixing and milling of active ingredients and auxiliaries (5% DISPERSOGEN®1494; 8% SIPERNAT®622S, Kaolin (balance to 100 g) under compressed air.

For example,
The crystalline modification I of mesotrione 60%
The crystalline modification I of halosulfuron-methyl 12%
DISPERSOGEN®1494 5%
SIPERNAT®622S (Silicon dioxide) 8%
Kaolin balance to 100 g Formulations were prepared according to the methods above (Table A):

TABLE A

| Formulation | | Mesotrione (%) | | Halosulfuron-methyl (%) | |
|---|---|---|---|---|---|
| No | type | I | II | Amorphous | I |
| 1 | SC | 35 | / | / | / |
| 2 | SC | / | 35 | / | / |
| 3 | SC | / | / | 18 | / |
| 4 | SC | / | / | / | 18 |
| 5 | SC | 35 | / | 18 | / |

TABLE A-continued

| Formulation | | Mesotrione (%) | | Halosulfuron-methyl (%) | |
|---|---|---|---|---|---|
| No | type | I | II | Amorphous | I |
| 6 | SC | / | 35 | 18 | / |
| 7 | SC | 35 | / | / | 18 |
| 8 | SC | / | 35 | / | 18 |
| 9 | WP | 60 | / | / | 12 |
| 10 | SC | 30 | / | / | 19.5 |
| 11 | WG | 48 | / | / | 12 |
| 12 | SC | 15 | / | / | 26 |
| 13 | OD | 25 | / | / | 2 |
| 14 | WG | 40 | / | / | 20 |
| 15 | SC | 20 | / | / | 40 |

Biological Examples 1

A synergistic effect exists with a combination of two active compounds when the activity of a composition comprising both active compounds is greater than the sum of the activities of the two active compounds applied individually.

The expected activity for a given combination of two active compounds can be calculated by the so called "Colby equation" (see S. R. Colby, "Calculating Synergistic and Antagonistic Responses of Herbicide Combinations", Weeds 1967, 15, 20-22):

whereby:

A=the activity percentage of compound A when active compound A is employed at an application rate of m g/ha;

B=the activity percentage of compound B when active compound B is employed at an application rate of n g/ha;

E=the percentage of estimated activity when compounds A and B are employed together at an application rate of m g/ha and n g/ha;

then:

$$E = A + B - (A \times B / 100).$$

If the actual activity observed for the combination of compounds A and B is greater than that calculated, then the activity of the combination is superadditive. In other words, synergism is present.

Corn, sorghum, apple, cotton, tomato, sugarcane plants were sown side by side in the field. Different types of weeds and their relative density were recorded and are listed in Table 1 below. Formulations of Examples 1 to 8 above were applied 50 days after planting. After spraying the plants, the beds were maintained for about 2 weeks. Two weeks after application, the beds were examined to determine the efficiency of the treatment. The results are set forth below in Table 2 below.

TABLE 1

| Type of weed | |
|---|---|
| Type of weed | Relative density (%) |
| Annual kyllinga (*Kyllinga sesquiflorus*) | 10 |
| Chickweed (*Stellaria* media) | 15 |
| Deadnettle, purple (*Lamium purpureum*) | 5 |
| Lambsquarters, common (*Chenopodium* album) | 15 |
| Morningglory, ivyleaf (*Ipomoea hederacea*) | 20 |
| Ragweed, common (*Ambrosia artemisiifolia*) | 5 |
| Sea clubrush (*Bolboschoenus maritimus*) | 30 |

TABLE 2

| | | | Efficiency (%) | | | | | | |
|---|---|---|---|---|---|---|---|---|---|
| | | | | Efficiency Type of weed | | | | | |
| Formulation Examples | Mesotrione (g/ha) | Halosulfuron-methyl (g/ha) | *Kyllinga sesquiflorus* | *Stellaria media* | *Lamium purpureum* | *Chenopodium album* | *Ipomoea hederacea* | *Ambrosia artemisiifolia* | *Bolboschoenus maritimus* |
| Untreated | 0 | 0 | 0 | 0 | 0 | 0 | 0 | 0 | 0 |
| Example 1 | 122.5 | 0 | 20 | 30 | 25 | 30 | 25 | 25 | 30 |
| Example 2 | 122.5 | 0 | 15 | 30 | 30 | 30 | 30 | 25 | 30 |
| Example 3 | 0 | 63 | 30 | 35 | 30 | 30 | 30 | 25 | 30 |
| Example 4 | 0 | 63 | 35 | 40 | 35 | 35 | 40 | 30 | 35 |
| Example 5 | 122.5 | 63 | 80 | 75 | 70 | 75 | 85 | 80 | 80 |
| Example 6 | 122.5 | 63 | 65 | 70 | 65 | 60 | 75 | 65 | 70 |
| Example 7 | 122.5 | 63 | 95 | 100 | 95 | 90 | 100 | 95 | 95 |
| Example 8 | 122.5 | 63 | 75 | 80 | 85 | 75 | 80 | 75 | 85 |

Biological Example 2

Rice plants were sown side by side in the field. Different types of weeds and their relative density were recorded and are listed in Table 3 below. Formulations of Examples 9 to 15 above were applied 50 days after planting. After spraying the plants, the beds were maintained for about 2 weeks. Two weeks after application, the beds were examined to determine the efficiency of the treatment. The results are set forth below in Table 4 below.

TABLE 3

| Type of weed | |
|---|---|
| Type of weed | Relative density (%) |
| Cockspur (*Echinochola crusgalli*) | 10 |
| Horsetail (*Equisetum arvense*) | 5 |
| MULLUMBIMBY COUCH (*Cyperus brevifolus*) | 10 |
| Mustard, wild (*Sinapis arvensis*) | 10 |
| NUTGRASS (*Cyperus rotundus*) | 15 |
| Nutsedge, yellow (*Cyperus esculentus*) | 10 |
| Pigweed, Redroot (*Amaranthus retroflexus*) | 15 |
| Pigweed, smooth (*Amaranthus hybridus*) | 20 |
| Velvetleaf (*Abutilon theophrasti*) | 5 |

TABLE 4

| Formulation Examples | Mesotrione (g/ha) | Halosulfuron-methyl (g/ha) | Echinochola crusgalli | Equisetum arvense | Cyperus brevifolus | Sinapis arvensis | Cyperus rotundus | Cyperus esculentus | Amaranthus retroflexus | Amaranthus hybridus | Abutilon theophrasti |
|---|---|---|---|---|---|---|---|---|---|---|---|
| Untreated | 0 | 0 | 0 | 0 | 0 | 0 | 0 | 0 | 0 | 0 | 0 |
| Example 9 | 150 | 30 | 95 | 100 | 95 | 95 | 100 | 100 | 95 | 90 | 100 |
| Example 10 | 100 | 65 | 100 | 100 | 100 | 95 | 100 | 100 | 100 | 100 | 95 |
| Example 11 | 150 | 37.5 | 100 | 95 | 100 | 100 | 100 | 100 | 100 | 90 | 100 |
| Example 12 | 75 | 130 | 100 | 100 | 100 | 95 | 100 | 100 | 100 | 95 | 100 |
| Example 13 | 250 | 20 | 95 | 100 | 95 | 100 | 100 | 95 | 100 | 100 | 100 |
| Example 14 | 100 | 50 | 100 | 95 | 100 | 100 | 100 | 100 | 95 | 100 | 95 |
| Example 15 | 50 | 100 | 90 | 90 | 95 | 90 | 90 | 90 | 95 | 95 | 90 |

Biological Example 3

Turf was sown. Different types of weeds and their relative density were recorded and are listed in Table 5 below. Formulations of Examples 9 to 15 above were applied 50 days after planting. After spraying the plants, the beds were maintained for about 2 weeks. Two weeks after application, the beds were examined to determine the efficiency of the treatment. The results are set forth below in Table 6 below.

TABLE 5

| Type of weed | Relative density (%) |
|---|---|
| Cyperus brevifolus | 40 |
| Cyperus rotundus | 60 |

TABLE 6

| Formulation Examples | Mesotrione (g/ha) | Halosulfuron-methyl (g/ha) | Cyperus brevifolus | Cyperus rotundus |
|---|---|---|---|---|
| Untreated | 0 | 0 | 0 | 0 |
| Example 9 | 150 | 30 | 95 | 100 |
| Example 10 | 100 | 65 | 100 | 100 |
| Example 11 | 150 | 37.5 | 100 | 100 |
| Example 12 | 75 | 130 | 100 | 100 |
| Example 13 | 250 | 20 | 95 | 95 |
| Example 14 | 100 | 50 | 100 | 100 |
| Example 15 | 50 | 100 | 95 | 90 |

The invention claimed is:

1. A composition comprising a herbicidally effective amount of
   (A) the crystalline modification I of 2-(4-mesyl-2-nitrobenzoyl)cyclohexane-1,3-dione (mesotrione); and
   (B) the crystalline modification I of methyl 3-chloro-5-(4,6-dimethoxypyrimidin-2-ylcarbamoylsulfamoyl)-1-methylpyrazole-4-carboxylate (halosulfuron-methyl), wherein the crystal modification I of halosulfuron-methyl is crystallized using xylene and/or methyl ethyl ketone, and the crystal modification I of halosulfuron-methyl has an XRD spectrum that includes each of the following reflexes as 2θ values in an X-ray powder diffractogram recorded using Cu-Kα radiation at 25° C.:

$2\theta = 8.80 \pm 0.2$ (1)

$2\theta = 13.48 \pm 0.2$ (2)

$2\theta = 13.72 \pm 0.2$ (3)

$2\theta = 16.20 \pm 0.2$ (4)

$2\theta = 17.71 \pm 0.2$ (5)

$2\theta = 18.61 \pm 0.2$ (6)

$2\theta = 20.48 \pm 0.2$ (7)

$2\theta = 21.38 \pm 0.2$ (8)

$2\theta = 22.60 \pm 0.2$ (9)

$2\theta = 24.71 \pm 0.2$ (10)

$2\theta = 25.53 \pm 0.2$ (11)

$2\theta = 25.83 \pm 0.2$ (12)

$2\theta = 26.53 \pm 0.2$ (13)

$2\theta = 26.72 \pm 0.2$ (14).

2. The composition according to claim 1, wherein the weight ratio of (A) to (B) is in the range of from about 99:1 to about 1:99.

3. The composition according to claim 2, wherein the weight ratio of (A) to (B) is in the range of from 40:1 to about 1:40.

4. The composition according to claim 3, wherein the weight ratio of (A) to (B) is in the range of from 20:1 to 1:5.

5. The composition according to claim 1, wherein the total amount of (A) and (B) is from 5% to 99% by weight of the composition.

6. The composition according to claim 5, wherein the composition comprises, by weight, from about 1% to about 90% of (A) and from about 1% to about 90% of (B).

7. The composition according to claim 5, wherein the composition comprises, by weight, from about 1% to about 70% of (A) and from about 1% to about 70% of (B).

8. The composition according to claim 1, further comprising one or more auxiliaries selected from extenders, carriers, solvents, surfactants, stabilizers, anti-foaming agents, anti-freezing agents, preservatives, antioxidants, colorants, thickening agents, solid adherents, fillers, wetting agents, dispersing agents, lubricants, anticaking agents and diluents.

9. The composition according to claim 1, being formulated as a water-soluble concentrate (SL), an emulsifiable concentrate (EC), an emulsion, oil in water (EW), a microemulsion (ME), a suspension concentrate (SC), an oil-based suspension concentrate (OD), a flowable suspension (FS), a water-dispersible granule (WG), a water-soluble granule (SG), a wettable powder (WP), a water soluble powder (SP), a granule (GR), an encapsulated granule (CG), a fine granule (FG), a macrogranule (GG), an aqueous suspo-emulsion (SE), a capsule suspension (CS) or a microgranule (MG).

10. A method of controlling undesirable plant growth in crops comprising applying to the plant or to the locus thereof a herbicidally effective amount of the herbicidal composition of claim 1.

11. The method according to claim 10, wherein the plant growth is being controlled in a crop comprising cereals, fruits, fibrous plants, vegetables, sugarcane and turf.

12. The method according to claim 10, wherein the plant growth being controlled is of one or more of perennial weeds, broadleaved weeds, grasses and sedges.

13. The method according to claim 12, wherein the plant growth being controlled is one or more of *Abutilon* spp., *Amaranthus* spp., *Ambrosia* spp., *Bolboschoenus* spp., *Chenopodium* spp., *Cyperus* spp., *Echinochola* spp., *Equisetum* spp., *Ipomoea* spp., *Kyllinga* spp., *Lamium* spp., *Sinapis* spp., *Stellaria* spp.

14. The method according to claim 10, wherein the composition is applied at an application rate of about 0.005 kilograms/hectare (kg/ha) to about 5.0 kg/ha of the total amount of active ingredient (A) and (B) being applied.

15. The method according to claim 14, wherein the composition is applied at an application rate of from about 0.01 kg/ha to about 3.0 kg/ha of the total amount of active ingredient (A) and (B) being applied.

16. The method according to claim 15, wherein the composition is applied at an application rate of from 1 to 1000 g/ha of (A) and from 1 to 500 g/ha of (B).

17. The method according to claim 16, wherein the composition is applied at an application rate of from 1 to 500 g/ha of (A) and 5 to 200 g/ha of (B).

18. The method according claim 10, wherein the composition is applied pre-planting, pre-emergence and/or post-emergence.

19. A method of controlling undesirable plant growth at a locus comprising applying to the locus herbicidally effective amounts of (A) the crystalline modification I of 2-(4-mesyl-2-nitrobenzoyl)cyclohexane-1,3-dione (mesotrione) and (B) the crystalline modification I of methyl 3-chloro-5-(4,6-dimethoxypyrimidin-2-ylcarbamoylsulfamoyl)-1-methyl-pyrazole-4-carboxylate (halosulfuron-methyl), wherein the crystal modification I of halosulfuron-methyl is crystallized using xylene and/or methyl ethyl ketone, and the crystal modification I of halosulfuron-methyl has an XRD spectrum that includes each of the following reflexes as 2θ values in an X-ray powder diffractogram recorded using Cu-Kα radiation at 25° C.:

$2\theta = 8.80 \pm 0.2$ (1)

$2\theta = 13.48 \pm 0.2$ (2)

$2\theta = 13.72 \pm 0.2$ (3)

$2\theta = 16.20 \pm 0.2$ (4)

$2\theta = 17.71 \pm 0.2$ (5)

$2\theta = 18.61 \pm 0.2$ (6)

$2\theta = 20.48 \pm 0.2$ (7)

$2\theta = 21.38 \pm 0.2$ (8)

$2\theta = 22.60 \pm 0.2$ (9)

$2\theta = 24.71 \pm 0.2$ (10)

$2\theta = 25.53 \pm 0.2$ (11)

$2\theta = 25.83 \pm 0.2$ (12)

$2\theta = 26.53 \pm 0.2$ (13)

$2\theta = 26.72 \pm 0.2$ (14).

20. The method according to claim 19, wherein the plant growth is being controlled in a crop comprising cereals, fruits, fibrous plants, vegetables, sugarcane and turf.

21. The method according to claim 19, wherein (A) and (B) are applied to the locus at the same time.

22. The method according to claim 19, wherein (A) and (B) are applied to the locus consecutively.

23. The method according to claim 19, wherein the plant growth being controlled is of one or more of perennial weeds, broadleaved weeds, grasses and sedges.

24. The method according to claim 23, wherein the plant growth being controlled is one or more of *Abutilon* spp., *Amaranthus* spp., *Ambrosia* spp., *Bolboschoenus* spp., *Chenopodium* spp., *Cyperus* spp., *Echinochola* spp., *Equisetum* spp., *Ipomoea* spp., *Kyllinga* spp., *Lamium* spp., *Sinapis* spp., *Stellaria* spp.

25. The method according to claim 19, wherein the weight ratio of (A) to (B) applied is in the range of from about 99:1 to about 1:99.

26. The method according to claim 25, wherein the weight ratio of (A) to (B) applied is in the range of from about 80:1 to about 1:80.

27. The method according to claim 26, wherein the weight ratio of (A) to (B) applied is in the range of from about 20:1 to about 1:5.

28. The method according to claim 19, wherein (A) and (B) are applied at an application rate of about 0.005 kilograms/hectare (kg/ha) to about 5.0 kg/ha of the total amount of active ingredient (A) and (B) being applied.

29. The method according to claim 28, wherein (A) and (B) are applied at an application rate of from about 0.01 kg/ha to about 3.0 kg/ha of the total amount of active ingredient (A) and (B) being applied.

30. The method according to claim 29, wherein (A) and (B) are applied at an application rate of from 1 to 1000 g/ha of (A) and from 1 to 500 g/ha of (B).

31. The method according to claim 30, wherein (A) and (B) are applied at an application rate of from 1 to 500 g/ha of (A) and 5 to 200 g/ha of (B).

32. The method according to claim 19, wherein (A) and (B) are applied pre-planting, pre-emergence and/or post-emergence.

* * * * *